United States Patent [19]

Segawa et al.

[11] Patent Number: 5,312,426
[45] Date of Patent: May 17, 1994

[54] SURGICAL CLIP

[75] Inventors: Hiromu Segawa, Fujinomiya; Satoshi Sasaoka, Tokyo, both of Japan

[73] Assignee: Mizuho Ika Kogyo Kabushiki Kaisha, Tokyo, Japan

[21] Appl. No.: 31,232

[22] Filed: Mar. 12, 1993

[51] Int. Cl.5 .............................................. A61B 17/00
[52] U.S. Cl. .................................... 606/158; 606/157; 24/545
[58] Field of Search ............................... 606/157–158; 24/499, 547, 551, 563, 545, 546, 509, 510

[56] References Cited

U.S. PATENT DOCUMENTS

| | | | |
|---|---|---|---|
| 3,827,438 | 8/1974 | Kees | 606/158 |
| 4,192,315 | 3/1980 | Hilzinger et al. | 606/158 |
| 4,324,248 | 4/1982 | Perlin | 606/158 |
| 4,337,774 | 6/1982 | Perlin | 606/158 |
| 4,360,023 | 11/1982 | Sugita | 128/325 |
| 4,708,140 | 11/1987 | Baron | 606/158 |
| 4,961,743 | 10/1990 | Kees, Jr. et al. | 606/158 |

FOREIGN PATENT DOCUMENTS 4-68943  11/1992  Japan .

*Primary Examiner*—Peter A. Aschenbrenner
*Assistant Examiner*—Gary Jackson
*Attorney, Agent, or Firm*—Ladas & Parry

[57] ABSTRACT

A cerebral aneurysm clip used for clamping an intercerebral blood vessel during a surgical operation. The clip has a pair of opposite clamping blades or arms for clamping a blood vessel, semi-circular engagement portions integrally connected to the proximal ends of the clamping arms, and a resilient wire portion integrally connecting the two engagement portions for exerting a resilient clamping force to the clamping arms via the engagement portions. The clamping arms are opened and closed by manipulating forceps which has at its tip engagement protrusions engaging the engagement portions from the inside. In order to prevent a blood vessel from passing excessively beyond the region between the opposite clamping arms, a U-shaped wire element is attached to the clip. The wire element has a transverse section passed through and across the proximal ends of the clamping arms for preventing ingress of the blood vessel into the space between the engagement portions. The wire element has also a pair of connecting sections connecting the ends of the transverse section with the resilient portion of the clip. The connecting sections prevent a blood vessel from being caught by the resilient portion.

5 Claims, 4 Drawing Sheets

SURGICAL CLIP

BACKGROUND OF THE INVENTION

The present invention relates to a surgical clip and, more particularly, to a clip for clamping a blood vessel to blockade, for example, a cerebral aneurysm in a surgical operation.

A cerebral aneurysm clip is a surgical instrument for clamping the base part of a cerebral aneurysm to isolate the latter from the cerebral artery. A typical cerebral aneurysm clip comprises a coiled intermediate portion and a pair of arms integrally extending therefrom in substantially the same direction to form opposite clamping jaws for clamping a blood vessel, as disclosed in U.S. Pat. No. 4,360,023 to Sugita et al.

A cerebral aneurysm can be formed at a variety of positions in intercerebral blood vessels, and an access to a position where the aneurysm exists must be made through an extremely narrow space. In order to enable such an access to the aneurysm, a combination of a clip and forceps was proposed in Japanese Patent Publication No. Hei 4-68943.

The clip proposed in this Japanese patent publication has a pair of opposing clamping arms for clamping a blood vessel. These clamping arms are arranged in a common plane. A pair of opposing engagement portions extend from the proximal ends of the clamping arms away from the arms, respectively. These engagement portions also lie in the same plane as the clamping arms. The engagement portions are of inwardly concave arcuate shape whereby the engagement portions form a substantially circular ring when the clip is closed. The two engagement portions are integrally connected by a resilient portion for urging the clamping arms in mutual abutting contact for clamping a blood vessel. The resilient portion is made up of a pair of resilient rounded wire sections each forming a convolution extending from each engagement portion at an angle to the plane mentioned above, and a resilient intermediate wire section integrally connecting the two rounded wire sections. The intermediate wire section is offset from the plane of the engagement portions.

When the clip is to be applied to a blood vessel, forceps is used to open and close the clamping arms. The forceps has on the tip ends thereof a pair of semicylindrical engaging protrusions which form a cylindrical shape combinedly when the tip ends of the forceps are closed. In a closed state of the tip ends, the cylindrically combined engaging protrusions are inserted into a space formed between the engagement portions of the clip. When the forceps is manipulated to cause the semicylindrical engaging protrusions to move apart, the engaging protrusions are engaged with the internal surfaces of the arcuate engagement portions to cause the engagement portions to move apart against the resiliency of the resilient portion of the clip whereby the clamping arms are opened and can be put on the blood vessel. Thereupon the clamping arms are closed to clamp the blood vessel by manipulating the forceps reversely.

This known clip is characterized in that its engagement portions can be engaged from the inside by the engaging protrusions of the forceps, to open and close the clamping arms. In the case of the clip of the U.S. patent referred to before, the engagement portions of the clip can be engaged only from the outside by relatively bulky engaging members of the forceps, so that the operator is prevented by the engaging members from viewing the clamping arms and the blood vessel to which is clamping arms are to be applied. However, in the case of the clip disclosed in the Japanese patent publication, the engaging members or protrusions of the forceps engage the engagement portions of the clip from the inside so that the engaging protrusions are small in size, thus allowing the operator to view the clamping arms and the blood vessel without being obstructed by the engaging protrusions.

The known clip described above, however, has a drawback in that when the clip is being moved to be applied to a blood vessel the clamping arms tend to move too far to such an extent that the blood vessel passes beyond the area of the clamping arms and enters the space between the engagement portions. Should this occur, the clip will not be able to clamp the blood vessel correctly between its clamping arms. This must be avoided.

Furthermore, in this known clip, there is a possibility that a blood vessel other than a blood vessel to be clamped by the clamping arms is caught in the angular area between the rounded wire sections and the intermediate joining wire sections mentioned before while the clip is being advanced toward the blood vessel to be clamped.

SUMMARY OF THE INVENTION

An object of the present invention is to provide a surgical clip which can prevent a blood vessel from passing beyond the area of the clamping arms into the space defined by the engagement portions and further can prevent a blood vessel from being caught in the resilient portion of the clip, while retaining the advantage of providing a good field of view of the clamping arms and a blood vessel during the use of the forceps.

According to the present invention, there is provided a surgical clip for clamping a blood vessel which comprises a pair of opposing clamping arms for clamping a blood vessel therebetween, the arms lying in a common plane and having distal ends and proximal ends, respectively, a pair of opposing engagement portions extending from the proximal ends of the clamping arms away from the same, respectively, the engagement portions lying in the plane and being of an inwardly concave arcuate shape so that the engagement portions define therebetween a space to receive engagement protrusions of forceps therein, a resilient portion integrally connecting ends of the engagement portions, remote from the clamping arms, for urging, via the engagement portions, the clamping arms in mutual abutting contact for clamping the blood vessel, and wire means slidably passed through the clamping arms across the same adjacent to the proximal ends, the wire means being connected to the resilient portion.

The manner in which the foregoing object is achieved by the present invention will become apparent from the following detailed description when read in conjunction with the accompanying drawings.

DESCRIPTION OF THE PREFERRED EMBODIMENT

Figure 1:
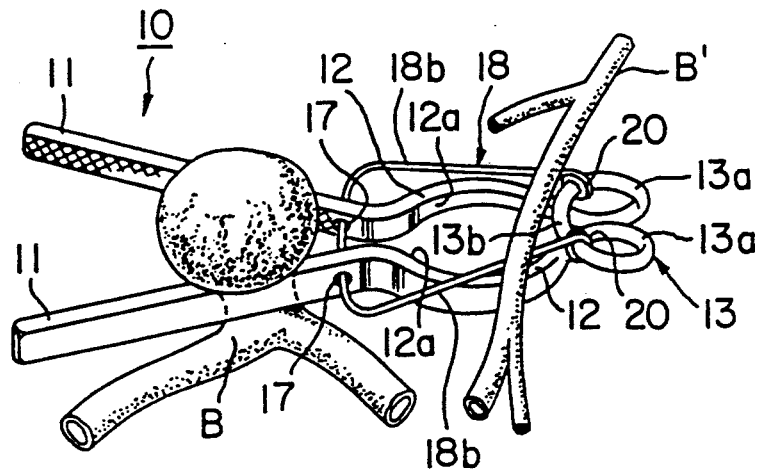
FIG. 1 is a perspective view showing a surgical clip according to an embodiment of the present invention.
Figure 2:
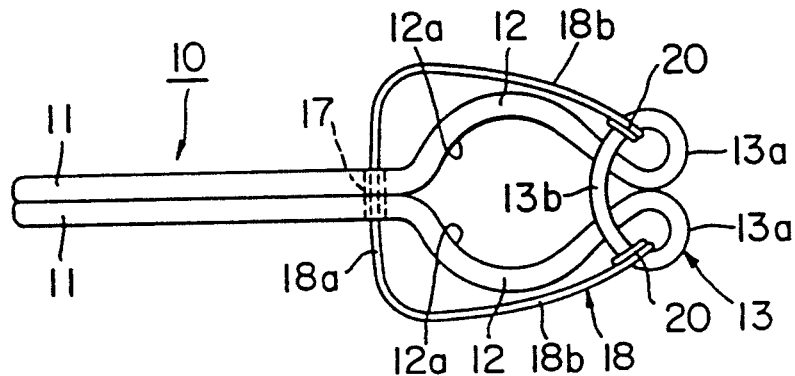
FIG. 2 is a top plan view of the clip shown in FIG. 1.
Figure 3:
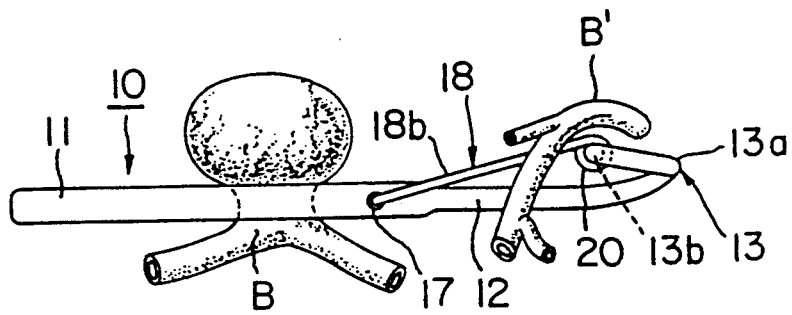
FIG. 3 is an elevational view of the clip shown in FIG. 1.

Referring first to FIGS. 1, 2 and 3, there is shown a surgical clip 10 for clamping a blood vessel according to the present invention. The clip 10 comprises a pair of blood clamping blades or arms 11 confronting each other. Backwardly from the proximal end of each of the blood clamping arms 11, integrally extends an engagement portion 12 intended to be engaged with a tip of a forceps as will be described later. The engagement portions 12 are formed so as to lie in an imaginary plane containing both the blood vessel clamping arms 11. The engagement portions 12 are each made of a resilient wire fashioned into an outwardly convex and inwardly concave arcuate shape, preferably, in the shape of an arc of a circle. Each of the engagement portions 12 has an inner arcuate surface serving as an engagement surface 12a adapted to be engaged with an engaging protrusion of the forceps described later.

The ends of the engagement portions 12, remote from the clamping arms 11, are coupled together by way of a resilient portion 13. The resilient portion 13 is made of a resilient wire integrally continuous with the rounded engagement portions 12, and includes a pair of resilient convolution outwardly from the corresponding engagement portion 12 and an intermediate joining sections 13b for integrally joining the pair of the rounded sections 13a. The joining section 13b is positioned outside or offset from the substantially circular region defined inside the engagement portion 12. It will be noted from FIG. 3 that the resilient portion 13 makes an angle with the plane of the clamping arms 11 and the engagement portions 12. The resilient portion 13 acts to exert a resilient force onto the engagement portions 12 so as to urge the confronting surfaces of the clamping arms 11 against each other.

Portions of the clamping arms 11 adjacent to the proximal ends thereof are formed with holes 17 as shown in FIG. 1. A substantially U-shaped wire element 18 is provided on the clip 10. The wire element 18 is made up of a transverse section 18a passed through the holes 17 and extending across the clamping arms 11, and a pair of connecting sections 18b located outside the engagement portions 12. The connecting sections 18b may be straight or slightly curved and have coiled ends 20 which are coiled around the rounded sections 13a or joining section 13b. It will be noted from FIG. 3 that the connecting sections 18b extend angularly to the plane of the clamping arms 11.

Figure 4:
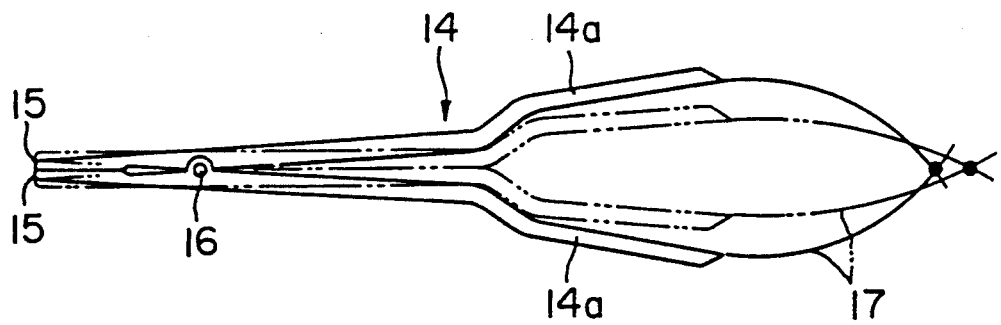
FIG. 4 is a plan view of forceps usable with the clip.

In order to apply the clip 10 to a blood vessel, forceps 14 shown in FIG. 4 is used. The forceps 14 has grips 14a which extend forward to form arms and are pivotally linked with each other through a pin 16 at their portions toward the forward ends. Furthermore, the grips 14a are biased away from each other by a spring 17. As a consequence, grasping portions 15 at the tips of a pair of opening/closing arms of the forceps are always subjected to forces causing them to approach each other.

Figure 5:
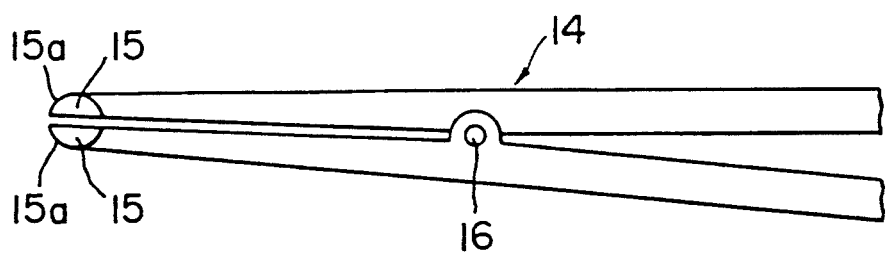
FIG. 5 is a partial enlarged view of the forceps shown in FIG. 4.
Figure 6:
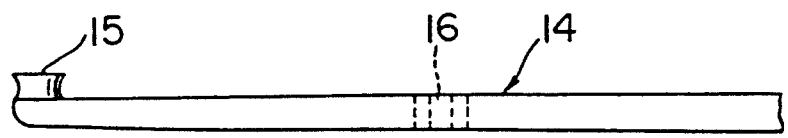
FIG. 6 is an elevational view of FIG. 5.

As shown in FIGS. 5 and 6, the grasping portions 15 of the forceps 14 are each in the form of an engagement protrusion and upstand from the tip of the forceps to the same side in parallel to the direction orthogonal to the plane along which the opening/closing arms of the forceps are swung. The engagement protrusions 15 are of a substantially semi-cylindrical configuration which in pairs form a substantially cylindrical shape, and each presents a substantially semi-cylindrical outer surface 15a. Each of the engagement protrusions 15 is concaved midway of the height thereof as indicated in FIG. 6 so as to be brought into surface contact with the engaging surface 12a provided inside the engagement portion 12. The concaved surface of each protrusion 15 is preferably made of a roughened surface.

In order to attach the clip 10 to the blood vessel, the forceps 14 being in the state shown in FIG. 4 are taken up. In this state, the tips of the forceps are closed as shown in FIG. 4, and the engagement protrusions 15 are closely located to form a substantially cylindrical configuration.

Figure 7:
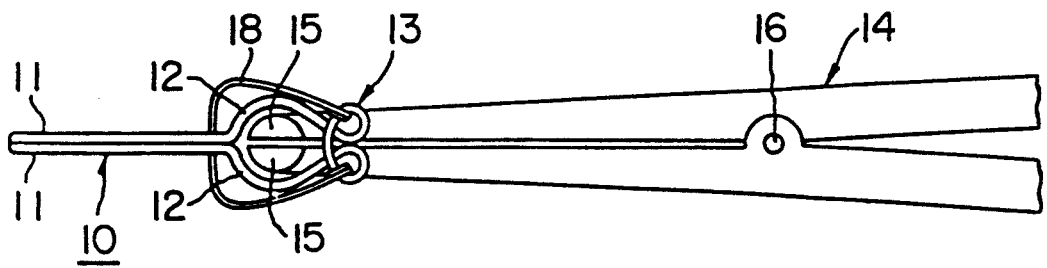
FIG. 7 is a plan view showing a state where the forceps is inserted into the clip.
Figure 8:
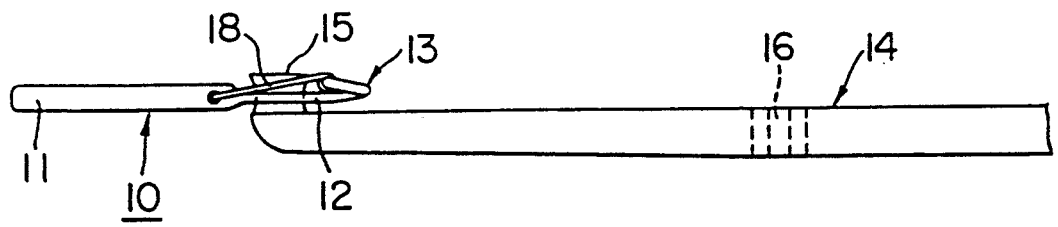
FIG. 8 is an elevational view of FIG. 7.
Figure 9:
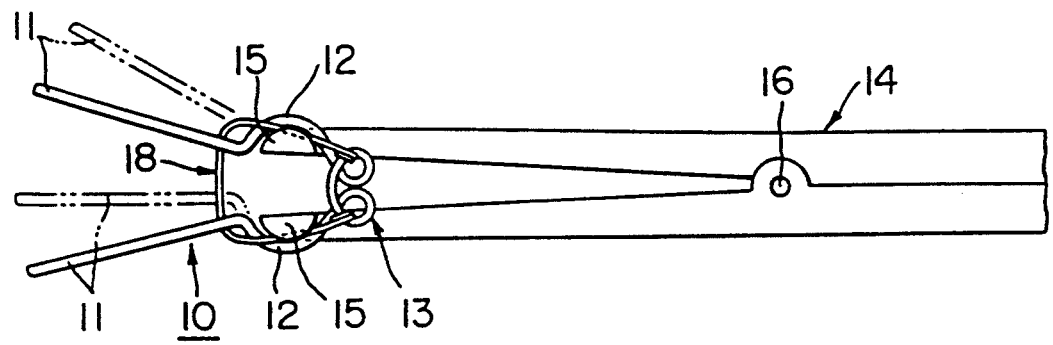
FIG. 9 is a plan view showing a state where blood vessel clamping arms are being opened by the forceps.
Figure 10:
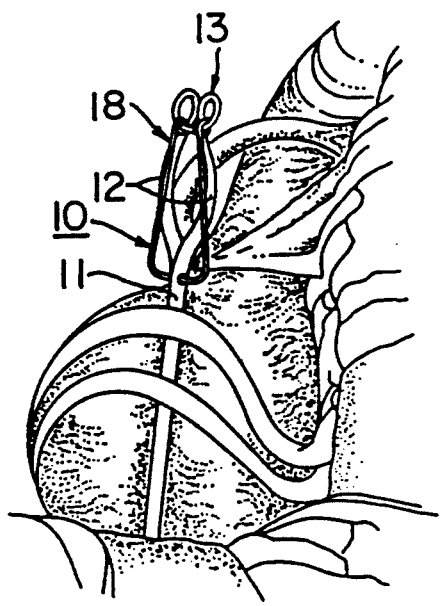
FIG. 10 illustrates a state in which the clip is applied to a blood vessel near a cerebral aneurysm.

With this state, the engagement protrusions 15 are inserted into the space between the engagement portions 12 of the clip as shown in FIGS. 7 and 8, and a gripping force is applied to the grips 14a. As a result, the tips of the forceps are opened, and the engagement protrusions 15 are displaced so as to be separated away from each other against the biasing force of the spring 17. As a result, the engagement protrusions 15 come into contact with the corresponding engagement surfaces 12a of the engagement portions 12 of the clip 10, to thereby elastically deform the engagement portions 12 outwardly as shown in FIG. 9, to consequently open the blood vessel clamping arms 11. The operator then advances the clip 11 grasped by the forceps 14 and then puts the clamping arms 11 on both sides of a blood vessel adjacent to a cerebral aneurysm. Then, the engagement protrusions 15 are caused to move closer to each other to the state shown in FIG. 7, whereupon the blood vessel clamping arms 11 of the clip are allowed to move toward each other by the resilient force of the resilient portion 13 to thereby clamp the blood vessel. When the forceps 14 is removed, the clip 10 is left on the blood vessel as illustrated in FIG. 10.

During the attachment of the clip as described above, the engagement portions 12 and the resilient portion 13 of the clip are not embraced from the outside by the tips of the forceps, and hence the blood vessel and the clamping arms 11 can be well viewed from the tail end side of the forceps, which results in a freedom from the problem obstructing the field of view as described earlier. This arises, in particular, from the fact that the engagement protrusions 15 are small and are allowed to project in only one direction orthogonal to the swinging surface of the forceps 14.

On the other hand, since the engagement portions 12 have the cylindrical inner surfaces and the engagement projections 15 have also the cylindrical surfaces, the clip 10 can be angularly adjusted as indicated in chain line in FIG. 9 while being held by the forceps, whereby the clamping arms 11 can be directed in a desired direction most suitable for placing the clamping arms 11 on both sides of a blood vessel.

When advancing the clamping arms 11 to both sides of a blood vessel, the clip 10 will not be advanced to such a degree that the blood vessel passes beyond the region of the clamping arms 11 into the space between the engagement portions 12 because the transverse section 18a of the wire element 18 will contact the blood vessel and function to prevent the clip 10 from advancing further. Thus the blood vessel B (FIG. 1) will be securely positioned and clamped between the clamping arms 11.

Figure 11:
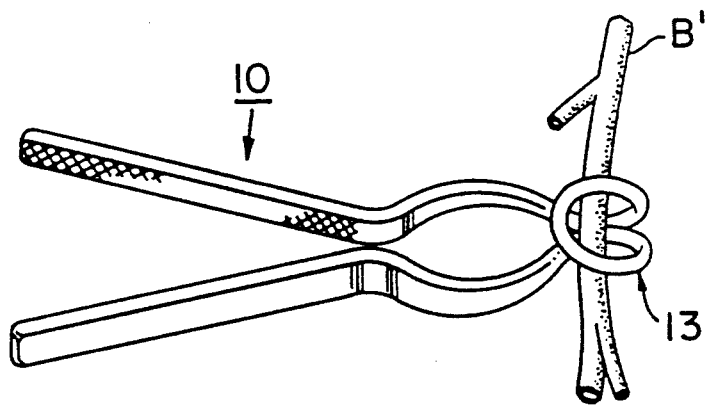
FIG. 11 is a perspective view of a know clip.

Furthermore, a possibility of another blood vessel B' being caught (see FIG. 11) in the angular space between the rounded wire sections 13a and the intermediate joining wire section 13b as indicated in FIGS. 1 and 3 can be eliminated because the connecting sections 18b of the wire element 18 prevents such blood vessel B' from moving relatively into such angular space.

Thus the improved clip according to the present invention can clamp a desired blood vessel correctly between its clamping blades or arms and can prevent a blood vessel from being caught in its resilient portion, due to the provision of the wire member, while retaining its advantage of providing a good field of view of the blood vessel and the clamping arms while using forceps for manipulating the clip.

What is claimed is:

1. A surgical clip for clamping a blood vessel comprising:
    a pair of opposing clamping arms for clamping a blood vessel therebetween, said arms lying in a common plane and having distal ends and proximal ends, respectively;
    a pair of opposing engagement portions extending from said proximal ends of the clamping arms away from the same, respectively, said engagement portions lying in said plane and being of an inwardly concave arcuate shape so that the engagement portions define therebetween a space to receive engagement protrusions of forceps therein;
    a resilient portion integrally connecting ends of said engagement portions, remote from said clamping arms, for urging, via said engagement portions, said clamping arms in mutual abutting contact for clamping the blood vessel; and
    wire means slidably passed through said clamping arms across the same adjacent to said proximal ends, said wire means being connected to said resilient portion.

2. The surgical clip according to claim 1, wherein said wire means is made up of a transverse section extending across said clamping arms, and a pair of connecting sections connecting both ends of said transverse section with said resilient portion.

3. The surgical clip according to claim 2, wherein each of said connecting sections has a coiled end which is coiled around said resilient portion.

4. The surgical clip according to claim 2, wherein said resilient portion comprises a pair of resilient rounded wire sections each forming a convolution extending from each said engagement portion at an angle to said plane, and a resilient intermediate joining section integrally connecting said rounded wire sections and extending in an offset relation to said plane.

5. The surgical clip according to claim 4, wherein each of said connecting sections has an end coiled around each of said rounded resilient wire sections so that the connecting sections extend at an angle to said plane.

* * * * *